(12) United States Patent
Holman et al.

(10) Patent No.: US 7,799,068 B2
(45) Date of Patent: Sep. 21, 2010

(54) ENDOVASCULAR APPARATUS

(75) Inventors: Thomas J. Holman, Minneapolis, MN (US); Darlene A. Thometz, Maple Grove, MN (US); Fertac Bilge, South Lake, TX (US); Paul J. Buscemi, Long Lake, MN (US); David H. Donabedian, Somerset, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 563 days.

(21) Appl. No.: 11/493,306

(22) Filed: Jul. 26, 2006

(65) Prior Publication Data

US 2006/0276881 A1 Dec. 7, 2006

Related U.S. Application Data

(60) Continuation of application No. 10/369,910, filed on Feb. 18, 2003, now abandoned, which is a continuation of application No. 10/003,218, filed on Oct. 30, 2001, now Pat. No. 6,692,523, which is a continuation of application No. 09/566,335, filed on May 8, 2000, now Pat. No. 6,319,276, which is a division of application No. 09/111,264, filed on Jul. 6, 1998, now Pat. No. 6,059,823, which is a division of application No. 08/600,834, filed on Feb. 13, 1996, now Pat. No. 5,871,537, application No. 11/493,306, and a continuation of application No. 10/842,745, filed on May 11, 2004, now abandoned, which is a continuation of application No. 10/288,185, filed on Nov. 5, 2002, now Pat. No. 7,491,230, which is a continuation of application No. 10/003,218, filed on Oct. 30, 2001, now Pat. No. 6,692,523, which is a continuation of application No. 09/566,335, filed on May 8, 2000, now Pat. No. 6,319,276, which is a division of application No. 09/111,264, filed on Jul. 6, 1998, now Pat. No. 6,059,823, which is a division of application No. 08/600,834, filed on Feb. 13, 1996, now Pat. No. 5,871,537.

(51) Int. Cl.
*A61F 2/06* (2006.01)
(52) U.S. Cl. ..................................... 623/1.25
(58) Field of Classification Search ................. 623/1.25, 623/1.11, 1.13, 1.23
See application file for complete search history.

(56) References Cited

U.S. PATENT DOCUMENTS 3,631,854 A 1/1972 Fryer (Continued)

FOREIGN PATENT DOCUMENTS

CA 2201320 4/1996

(Continued)

OTHER PUBLICATIONS

U.S. Appl. No. 10/454,896, filed Jun. 3, 2003, Holman et al.

*Primary Examiner*—Alvin J Stewart
(74) *Attorney, Agent, or Firm*—Vidas, Arrett & Steinkraus

(57) ABSTRACT

Percutaneous treatment of aortic aneurysms and like vascular anomalies by an apparatus and method wherein the apparatus is delivered via catheter and comprises a sleeve with at least one peripheral conduit which is caused to assume an expanded, rigid configuration by the introduction of a chemical or mechanical hardening means, whereby the sleeve is caused to assume an open cylindrical configuration for fluid flow therethrough.

22 Claims, 6 Drawing Sheets

U.S. PATENT DOCUMENTS

| | | | | |
|---|---|---|---|---|
| 3,991,767 | A | 11/1976 | Miller, Jr. et al. | |
| 4,141,364 | A | 2/1979 | Schultze | |
| 4,183,102 | A | 1/1980 | Guiset | |
| 4,271,839 | A | 6/1981 | Fogarty et al. | |
| 4,311,659 | A | 1/1982 | Rey et al. | 264/221 |
| 4,434,797 | A | 3/1984 | Silander | |
| 4,483,332 | A | 11/1984 | Rind | |
| 4,577,631 | A | 3/1986 | Kreamer | |
| 4,580,568 | A | 4/1986 | Gianturco | |
| 4,740,207 | A | 4/1988 | Kreamer | |
| 4,741,872 | A | 5/1988 | DeLuca et al. | |
| 4,762,132 | A | 8/1988 | Nicolas et al. | |
| 4,776,337 | A | 10/1988 | Palmaz | |
| 4,871,365 | A | 10/1989 | Dumican | |
| 5,123,917 | A | 6/1992 | Lee | |
| 5,151,105 | A | 9/1992 | Kwan-Gett | |
| 5,156,620 | A | 10/1992 | Pigott | |
| 5,234,456 | A | 8/1993 | Silvestini | 623/1 |
| 5,282,824 | A | 2/1994 | Gianturco | |
| 5,320,100 | A | 6/1994 | Herweck et al. | 623/1 |
| 5,328,471 | A | 7/1994 | Slepian | 604/101 |
| 5,330,528 | A | 7/1994 | Lazim | |
| 5,334,201 | A | 8/1994 | Cowan | |
| 5,336,178 | A | 8/1994 | Kaplan et al. | 604/53 |
| 5,370,691 | A | 12/1994 | Samson | |
| 5,411,549 | A | 5/1995 | Peters | 623/12 |
| 5,415,634 | A | 5/1995 | Glynn et al. | 604/96 |
| 5,423,851 | A | 6/1995 | Samuels | 606/198 |
| 5,443,495 | A | 8/1995 | Buscemi et al. | 623/1 |
| 5,464,419 | A | 11/1995 | Glastra | |
| 5,507,770 | A | 4/1996 | Turk | |
| 5,529,653 | A | 6/1996 | Glastra | |
| 5,534,024 | A | 7/1996 | Rogers et al. | 623/1.25 |
| 5,536,274 | A | 7/1996 | Neuss | |
| 5,554,119 | A | 9/1996 | Harrison et al. | |
| 5,554,180 | A | 9/1996 | Turk | |
| 5,556,426 | A | 9/1996 | Papadiuk et al. | 623/12 |
| 5,562,727 | A | 10/1996 | Turk et al. | |
| 5,676,685 | A | 10/1997 | Razavi | 606/194 |
| 5,716,397 | A | 2/1998 | Myers | |
| 5,725,547 | A | 3/1998 | Chuter | |
| 5,725,568 | A | 3/1998 | Hastings | 623/1 |
| 5,738,901 | A | 4/1998 | Wang et al. | 427/2.3 |
| 5,741,324 | A | 4/1998 | Glastra | |
| 5,766,203 | A | 6/1998 | Imran et al. | |
| 5,800,524 | A | 9/1998 | Borghi | |
| 5,800,538 | A | 9/1998 | Slepian et al. | |
| 5,871,537 | A | 2/1999 | Holman et al. | 623/1 |
| 5,908,435 | A | 6/1999 | Samuels | |
| 5,947,995 | A | 9/1999 | Samuels | |
| 6,007,575 | A | 12/1999 | Samuels | |
| 6,015,424 | A | 1/2000 | Rosenbluth et al. | 606/200 |
| 6,047,825 | A | 4/2000 | Samuels | |
| 6,053,943 | A | 4/2000 | Edwin et al. | 623/1.25 |
| 6,059,823 | A | 5/2000 | Holman et al. | |
| 6,159,230 | A | 12/2000 | Samuels | |
| 6,312,462 | B1 | 11/2001 | McDermott et al. | |
| 6,319,276 | B1 | 11/2001 | Holman et al. | |
| 6,355,063 | B1 | 3/2002 | Calcote | 623/1.42 |
| 6,395,019 | B2 | 5/2002 | Chobotov | |
| 6,428,566 | B1 | 8/2002 | Holt | 623/1.11 |
| 6,432,131 | B1 | 8/2002 | Ravenscroft | 623/1.13 |
| 6,588,588 | B2 | 7/2003 | Samuels | |
| 6,692,523 | B2 | 2/2004 | Holman et al. | 623/1.25 |
| 6,706,064 | B1 | 3/2004 | Anson | |
| 2002/0144920 | A1 | 10/2002 | Samuels | |
| 2003/0083738 | A1 | 5/2003 | Holman et al. | |
| 2003/0208257 | A1 | 11/2003 | Holman et al. | 623/1.11 |
| 2003/0220684 | A1 | 11/2003 | Holman et al. | |
| 2003/0225453 | A1 | 12/2003 | Murch | |

FOREIGN PATENT DOCUMENTS

| | | |
|---|---|---|
| CA | 2420638 | 8/1997 |
| CA | 2383428 | 3/2001 |
| CA | 2246355 | 4/2003 |
| DE | 28 05 749 A1 | 8/1978 |
| EP | 0 441 516 | 8/1991 |
| EP | 0 502 905 B1 | 9/1994 |
| EP | 0 617 930 | 10/1994 |
| EP | 0 664 107 A1 | 7/1995 |
| EP | 808613 | 11/1997 |
| WO | WO 89/09031 | 10/1989 |
| WO | WO 91/07927 | 6/1991 |
| WO | WO 95/08289 A2 | 3/1995 |
| WO | WO 96/10967 | 4/1996 |
| WO | WO 97/00073 | 1/1997 |
| WO | WO 97/03624 | 2/1997 |
| WO | WO 97/19653 | 6/1997 |
| WO | WO 97/29716 | 8/1997 |
| WO | WO 99/00073 | 1/1999 |

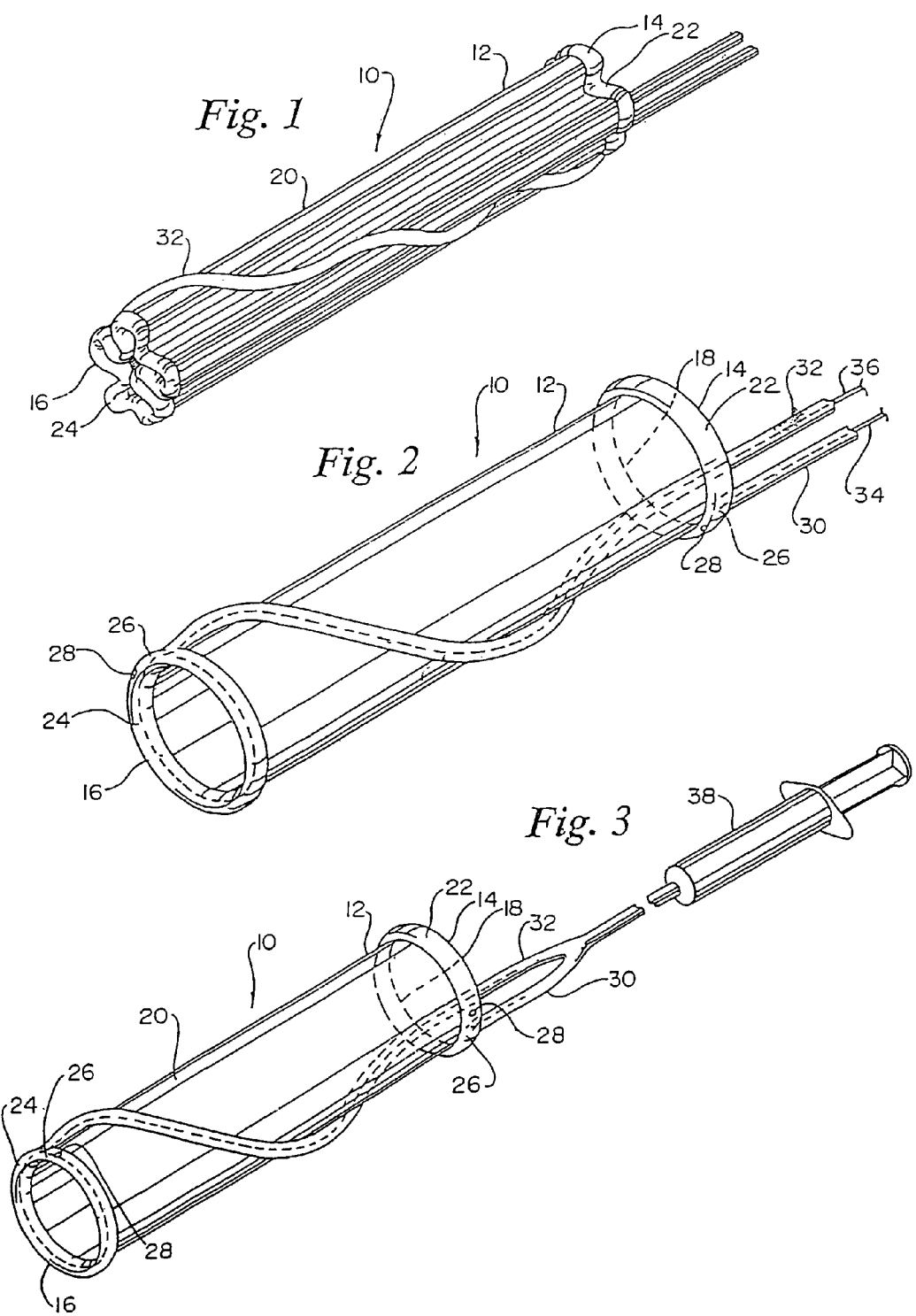

ENDOVASCULAR APPARATUS

CROSS-REFERENCE TO RELATED APPLICATIONS

This application is a continuation of U.S. patent application Ser. No. 10/369,910, filed on Feb. 18, 2003, now abandoned which is a continuation of Ser. No. 10/003,218, filed on Oct. 30, 2001 (now U.S. Pat. No. 6,692,523, which issued on Feb. 17, 2004), which is a continuation of U.S. patent application Ser. No. 09/566,335, filed on May 8, 2000 (now U.S. Pat. No. 6,319,276, which issued on Nov. 20, 2001), which is a divisional of U.S. patent application Ser. No. 09/111,264, filed on Jul. 6, 1998 (now U.S. Pat. No. 6,059,823, which issued on May 9, 2000), which is a divisional of U.S. patent application Ser. No. 08/600,834, filed on Feb. 13, 1996 (now U.S. Pat. No. 5,871,537, which issued on Feb. 16, 1999).

This Application is also a continuation of U.S. patent application Ser. No. 10/842,754 filed on May 11, 2004, now abandoned which is a continuation of Ser. No. 10/288,185 filed on Nov. 5, 2002, now U.S. Pat. No. 7,491,230 which is a continuation of Ser. No. 10/003,218, filed on Oct. 30, 2001 (now U.S. Pat. No. 6,692,523, which issued on Feb. 17, 2004), which is a continuation of U.S. patent application Ser. No. 09/566,335, filed on May 8, 2000 (now U.S. Pat. No. 6,319,276, which issued on Nov. 20, 2001), which is a divisional of U.S. patent application Ser. No. 09/111,264, filed on Jul. 6, 1998 (now U.S. Pat. No. 6,059,823, which issued on May 9, 2000), which is a divisional of U.S. patent application Ser. No. 08/600,834, filed on Feb. 13, 1996 (now U.S. Pat. No. 5,871,537, which issued on Feb. 16, 1999), all of which are incorporated herein by reference.

BACKGROUND OF THE INVENTION

1. Field of the Invention

The present invention relates to the percutaneous treatment of vessels by an apparatus and method wherein the apparatus is delivered via catheter and comprises a surgical graft which is fixated in a vessel by means of a chemical or mechanical hardening-filler material system.

2. General Background

Previous methods of treating aortic aneurysms include treatment via surgical procedure in which an incision is made in the abdomen or chest of the patient, the diseased area is cleaned by the surgeon and an artificial graft is sutured in place. This highly invasive procedure usually results in long hospital stays and lengthy recoveries. Further, mortality and morbidity complications often result as a consequence of this surgical procedure.

Other percutaneous methods have been attempted, such as are disclosed in U.S. Pat. No. 4,577,631 (utilizing occlusion catheters with pressure sensitive adhesives), U.S. Pat. No. 4,740,207 (self-expanding stent-type materials) and U.S. Pat. Nos. 4,271,839, 4,776,337 and 4,762,132 (other stent derived devices).

There still exists a need, however, for a simple method of repairing a vessel with an intravascular graft which allows normal tissue ingrowth to occur at the repair site. There exists a specific need for a percutaneous approach in which a catheter could be loaded with a surgical graft that can be fixated in a vessel such as the aorta.

SUMMARY OF THE INVENTION

The present invention provides devices for repairing aortic aneurysms and the like. The intraluminal graft of the present invention in one embodiment comprises a flexible linear or bifurcated tubular sleeve delivered to a repair site in a body by suitable means such as a catheter. The sleeve is suitably made of woven or cast material, and has peripheral conduits or tubes at each end. Each conduit has at least a single port that is connected to an elongated introduction means associated with the catheter delivery means. The introduction means may be attached to the outer surface of the sleeve. The collapsed sleeve may be made rigid and circular by the introduction through the introduction means of a chemical or mechanical hardening means.

The chemical hardening means may be a polymeric material introduced through the introduction means through an external source, such as a catheter or syringe. Alternatively, the mechanical hardening means may comprise a single wire or multiple wires inserted into the conduits to support the ends, or any portion of the sleeve. The wires are not attached to the sleeve but reside in the conduits to provide a constant spring tension. The wires may be of any suitable material which retains its tension, such as spring wire or memory wire.

The introduction means may be detached from the sleeve after introduction of the chemical or mechanical hardening means.

The sleeve may alternatively be associated with a fixation means comprising either a series of cylindrical tubules or an enclosure which fits over the sleeve, with a hardening-filler system enclosed therein. The hardening-filler system includes an activatable hardening material which may be provided in the form of microspheres that upon external agitation may be disrupted, allowing the contents to react together and form a hardened material that fills the tubules or enclosure, thereby expanding and rigidifying the fixation means, and fixing the sleeve in place in the site of repair. Polymeric materials which are activatable include thioisocyanates, aldehydes, isocyanates, divinyl compounds, epoxides or acrylates. In addition to the aforementioned, photoactivatable crosslinkable groups as succinimidyl azido salicylate, succinimidyl-atidobenzoate, succinimidyl dithio acetate, azidoiodobenzene, fluoro nitrophenylazide, salicylate azides, benzophenone-maleimide, and the like may be used as photoactivatable crosslinking reagents. The material may also consist of a thin coating which can be activated by external forces such as laser, radio frequency, ultrasound or the like, with the same hardening result taking place. These materials would allow for normal tissue ingrowth to take place.

BRIEF DESCRIPTION OF THE FIGURES

FIG. 1 shows a perspective view of a vascular graft according to the present invention in a folded state prior to placement and expansion thereof;

FIG. 2 shows a perspective view of the vascular graft in an expanded state by means of wires;

FIG. 3 is a perspective view of the device as in FIG. 2 showing the introduction of chemical hardening material via syringe;

DETAILED DESCRIPTION OF THE INVENTION

Figure 4:
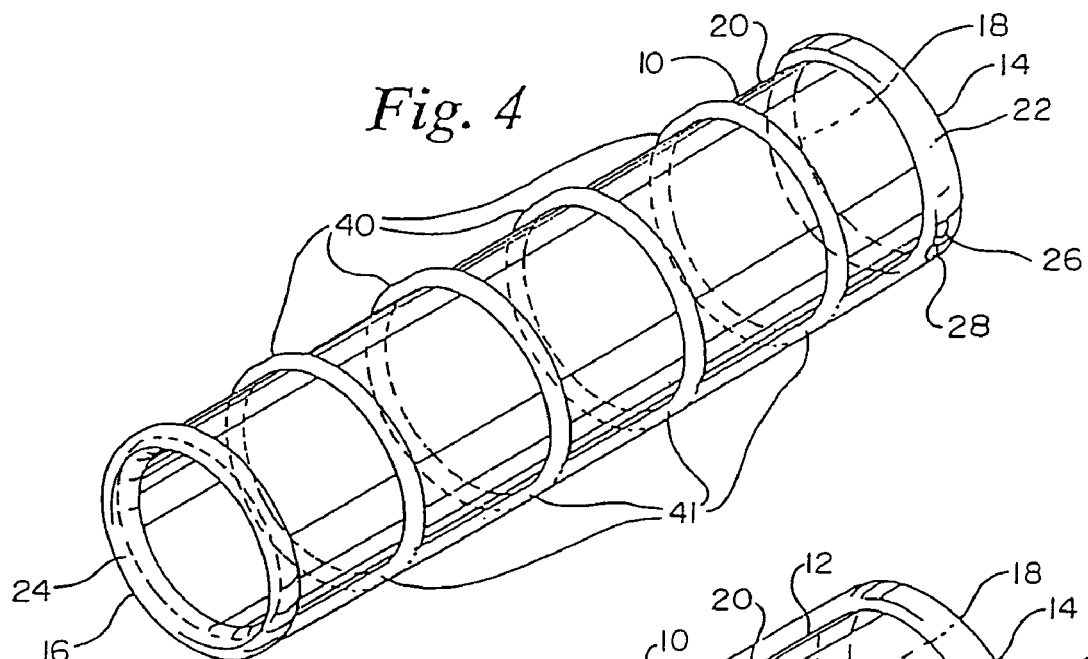
FIG. 4 is a perspective view of an alternate embodiment comprising a series of cylindrical tubules.

The present invention provides a device and method for repairing an aneurysm or the like in a vessel, such as the aorta.

Referring to FIGS. 1 and 2, a vascular graft comprising a sleeve is shown generally at 10. Sleeve 10 is shown in a folded conformation in FIG. 1 and in an expanded state in FIG. 2. Sleeve 10 is either a flexible linear or bifurcated (as shown in FIGS. 7-12) tubular sleeve made of woven or extruded cast material. Sleeve 10 is made of a biocompatible polymeric material. Fabrics from which sleeve 10 may be made are polyamides, such as nylon 6, nylon 6,6, and the like, Dacron®, polyesters, such as PET, polyethers, fluorinated polymers, such as polytetrafluoroethylene (PTFE), or biodegradable or nonbiodegradable fibers derived from natural sources such as carbohydrates, collagens, and proteins. The fabric may be of a woven knit, or solid structure. The most preferred materials are Dacron® and PTFE. Sleeve 10 is suitably delivered by a catheter. Catheters of polyurethane, PTFE, PVC silicone or the like with internal diameters of 1 to about 3 mm are suitable for polymer injection.

Sleeve 10 has a proximal end 14, a distal end 16, an interior portion 18, an exterior portion 20 and peripheral circular conduits or tubes 22,24 located one at each end 14,16, respectively. Each conduit 22,24 has at least one inlet port 26 and at least one outlet or exhaust port 28, inlet(s) 26 being connected to elongated introduction means 30,32 respectively. Introduction means 30,32 may be attached to exterior portion 18 of sleeve 10. Referring to FIG. 2, collapsed sleeve 10 is expanded and made rigid by the insertion of a spring wire or wires 34,36 inserted through introduction means 30,32. A single wire or multiple wires may be inserted to support ends 14,16, the center body or any portion of sleeve 10. Wires 34,36 are not attached to sleeve 10 but reside in introduction means 30,32 or conduits 22,24, providing a constant spring tension. The entrance tubing may be detached from the sleeve after placement of supporting wires 34,36 in end tubes 22,24.

The supporting wire may be made of stainless steel, spring steel, memory shape metals (such as nitinol, for example), titanium, or metal alloys of any kind, not limited to the aforementioned. Furthermore, the configuration of the supporting wire may be solid, braided or woven.

As shown in FIG. 3, the graft may be expanded and made rigid and circular by a chemical hardening means introduced into a single spiral tube, or alternatively, as shown in FIG. 4, a series of interconnected concentric cylindrical tubules 40 attached to and encasing the sleeve 10. Tubules 40 are interconnected by means of connecting tubes 41 extending between the tubules. The chemical hardening means may be introduced in the form of an injectable polymeric material comprised of a one part system, a two part system, self expanding systems, thermosets, thermoplastics and the like. These polymers or polymeric systems would fill tubes 32 or tubules 40, causing them to expand and rigidify, thereby fixing the sleeve at the site of repair. This embodiment is of particular use for fusing such grafts in large vessels such as the aorta or pulmonary arteries.

Two part activatable hardening material may be supplied in the form of microspheres (not shown) that upon agitation by an external force may be disrupted. The external energy could originate from any suitable source including IR, visible or UV light through optic fiber on mechanical vibrational means from about 1 to 100,000 hertz supplied by mechanical or electrical transducers or by heat upon disruption of the microspheres, the activatable hardening material is liberated and allowed to harden. Disruption of the microspheres releases the separated components, allowing the components to react together and form a hardened material that fills series of tubules 40 thereby fixing sleeve 10 in place at the site of repair. Polymeric systems may be comprised of vinyl or divinyl compounds in which an initiator is contained in the microspheres, epoxies containing microencapsulated amine component, or diisocyanates with encapsulated amine or hydroxyl terminated prepolymers. Amino groups can be so isolated from methylacetimidate, ethyl acetimidate, dimethylglutarimidate, dimethyl, adipidate, dimethyl sebainidate, diisothionyl propionimidate, dimethyl oxydipropionimidate-succinate bis-esters, disuccinimidyl tartarate, dicyanatobenzene, dichlorodinitrobenzene, adipaldehyde, glutaraldehyde and the like.

These hardening-filler systems would allow for normal tissue ingrowth in series of tubules 40 to take place. Because the tubules comprise only a small fraction of the total surface area of the sleeve, these hardening filling systems would allow for tissue ingrowth to take place into the sleeve material not impeded by the tubules, providing further reinforcement of the placement of the sleeve 10.

Figure 5:
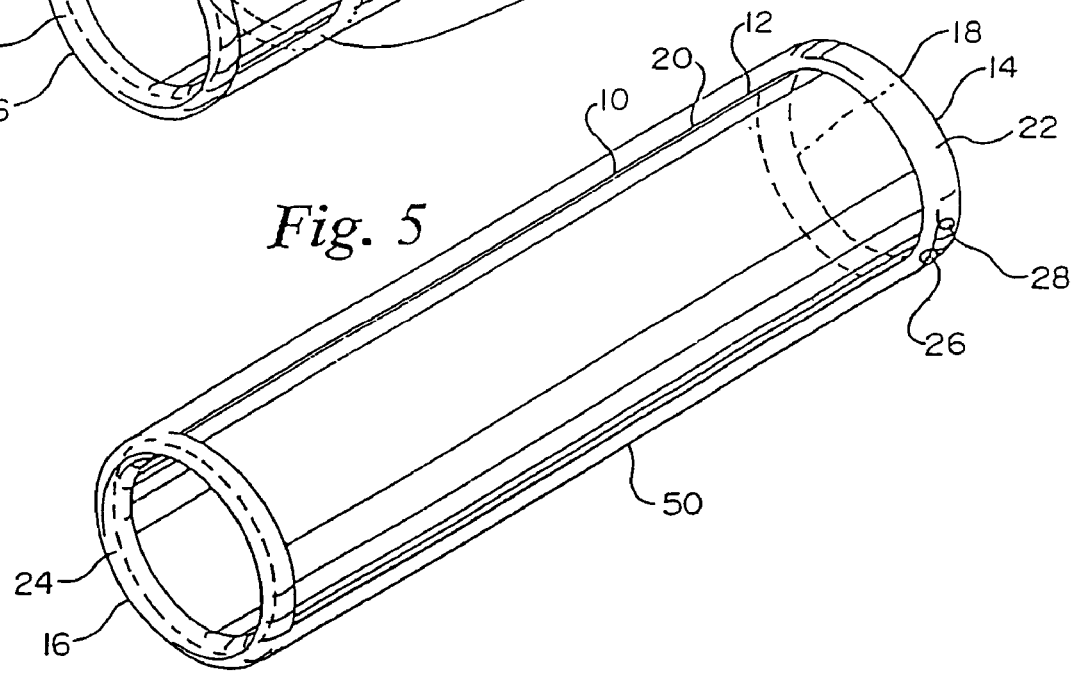
FIG. 5 is a perspective view of an alternative embodiment of the device, where the vascular graft includes an enclosure which fits over the sleeve.

In a further embodiment shown in FIG. 5, the material may be introduced by means of a hardening-filler system comprising an enclosure 50 attached to sleeve 10. Enclosure 50, like tubules 40, is filled with an activatable hardening material consisting of either a one-part polymer system, a two-part polymer system or a self-expanding monomer, which upon polymerization would fill enclosure 50, causing it to expand and rigidify, thereby fixing sleeve 10 at the site of repair. The activatable hardening material is described above with reference to FIG. 4.

Figure 6:
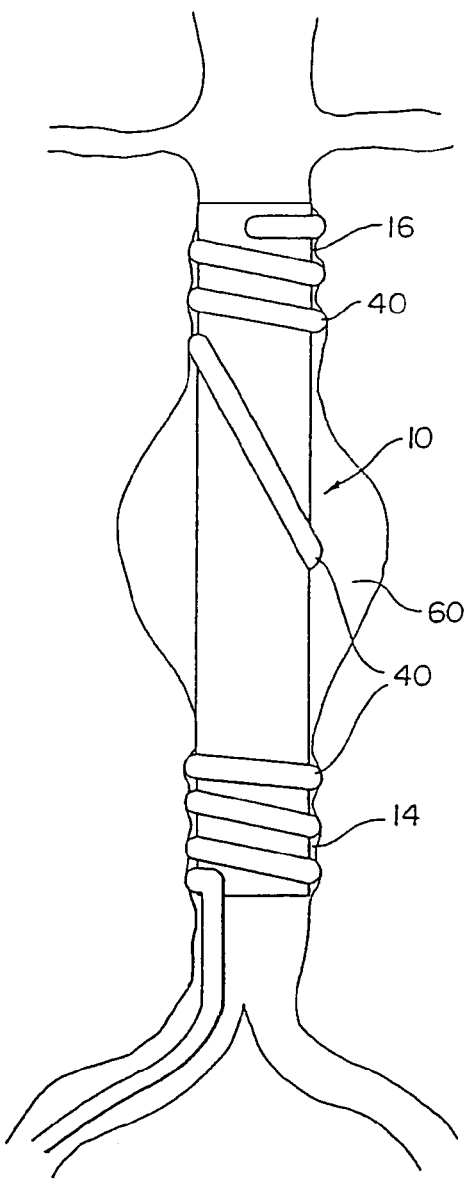
FIG. 6 is an alternative embodiment of the present invention having a fluid track comprising a continuous cylindrical tubule which is helically wound around the proximal and distal ends of the sleeve.

Referring now to FIG. 6, an alternative embodiment of sleeve 10 is shown in place at a repair site 60. Sleeve 10 has a fluid track comprising a continuous cylindrical tubule 40 which is helically wound around proximal end 14 and distal end 16 of sleeve 10. Tubule 40 can be filled with a curing polymer selected from thermoset polymers or two part polymers, as described hereinabove. Sleeve 10 may optionally include supplemental physical attachment means (not shown) such as spikes, barbs or the like at proximal and distal ends 14,16.

Figure 7A:
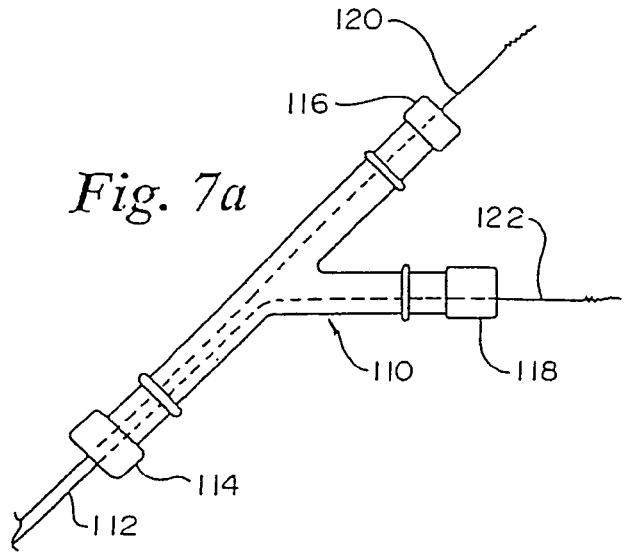
FIGS. 7a and 7b represent an alternative embodiment comprising a bifurcated vascular graft including a dual guide wire delivery system.
Figure 7B:
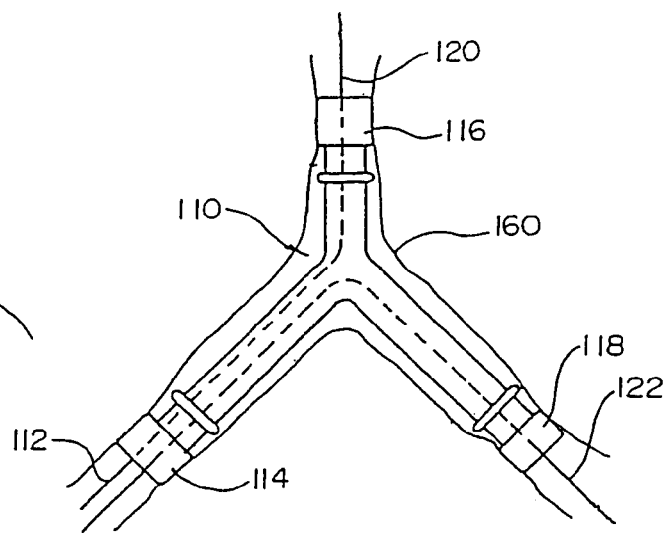
Figure 8A:
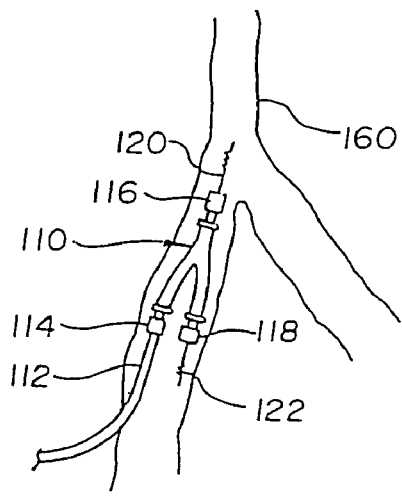
FIGS. 8a through 8d show placement of a bifurcated vascular graft according to the present invention.
Figure 8B:
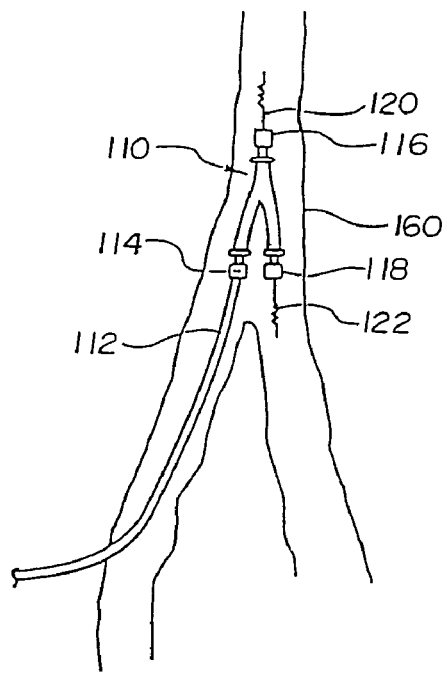
Figure 8C:
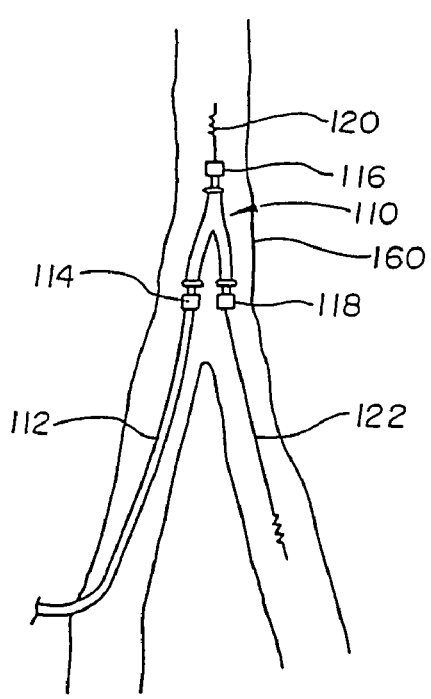
Figure 8D:
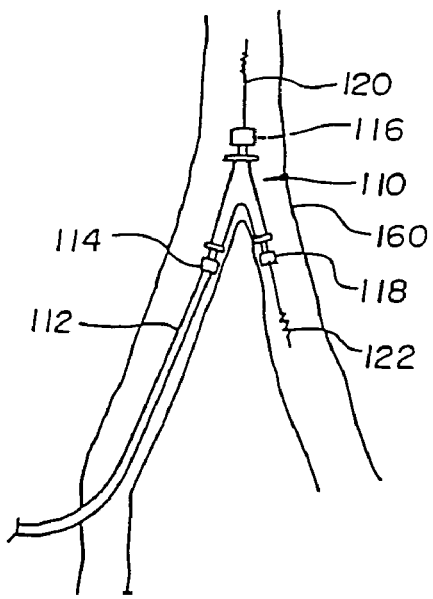
Figure 9:
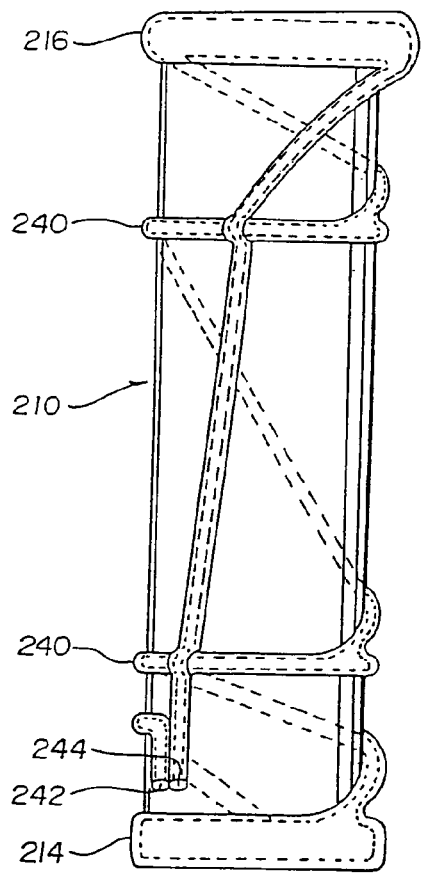
FIG. 9 shows a further alternative embodiment of a vascular graft according to the present invention.

FIGS. 7-9 represent an alternative embodiment comprising a bifurcated vascular graft 110 including a dual guide wire delivery system 112. Graft 110 has a proximal end 114 and at least two distal-ends 116,118. FIGS. 8a through 8d show placement of bifurcated vascular graft 110 at a repair site 160 where the vessel bifurcates. Graft 110 and delivery system 112 are advanced through a vessel to repair site 160. Delivery system 112 includes guide wires 120,122 whereby ends 114, 116,118 are placed at different branches of the vessel bifurcation. FIG. 7b shows graft 110 in place at site 160.

FIGS. 9-12 show an alternative embodiment of a vascular graft according to the present invention, indicated generally at 210. Graft 210 has proximal and distal ends 214,216 and cylindrical tubule 240. Tubule 240 has a first end 242 and a second end 244, located near proximal end 214. After placement of graft 210, tubule 240 is filled.

Figure 10A:
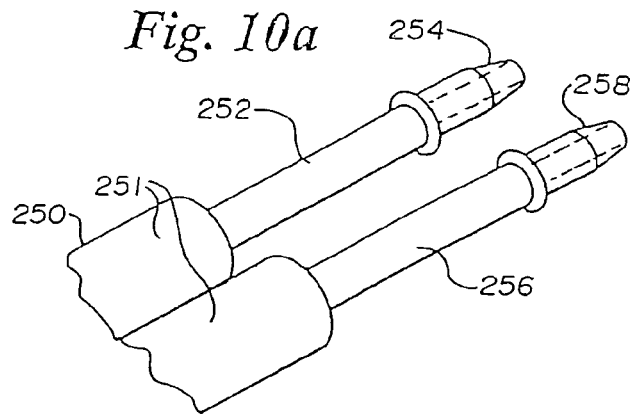
FIGS. 10a through 10c show filling of the cylindrical tubules after placement of the graft.
Figure 10B:
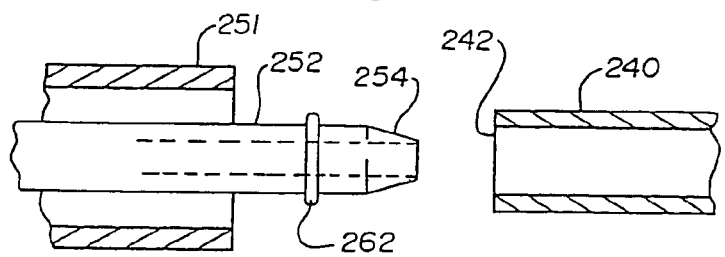
Figure 10C:
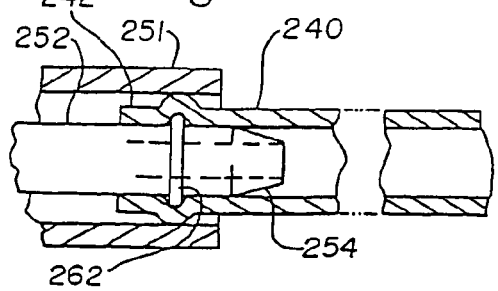
Figure 11A:
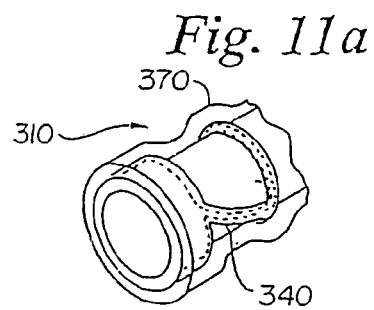
FIGS. 11a through 11d are fragmentary views of vascular grafts according to the present invention.
Figure 11B:
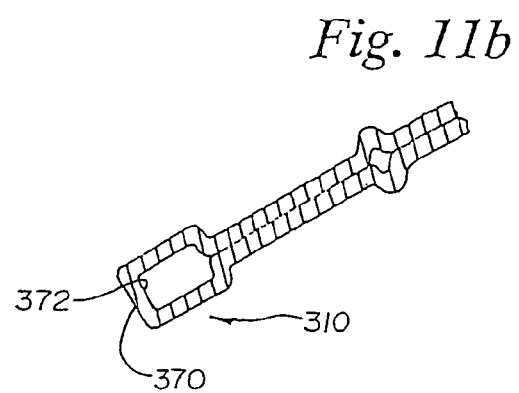
Figure 11C:
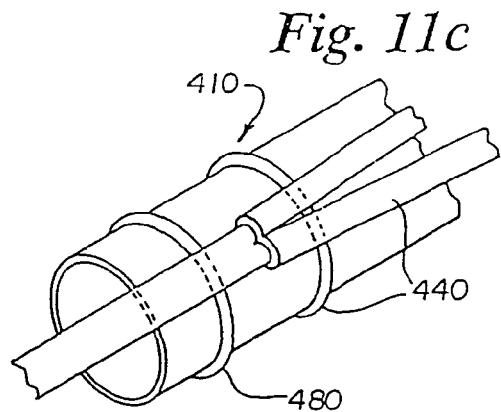
Figure 11D:
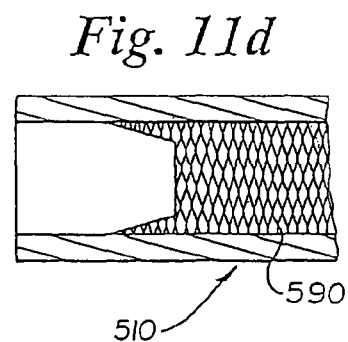

Referring to FIGS. 10a, 10b and 10c, filling means 250 is shown. Although filling means 250 is shown in conjunction with a tubular vascular graft, such a filling means may be used with any vascular graft according to the present invention. Filling means 250 comprises casing 251, filling tube 252 with distal infusion inlet 254 and exhaust tube 256 with distal exhaust vent 258. Filling means 250 may be incorporated into the vascular graft delivery means or may alternatively be separate from, but associated with the delivery means. FIG. 10b is an enlarged fragmentary view of filling tube 252 which shows the manner in which infusion inlet 254 connects to first end 242 of tubule 240, via pinch ring 262 located near the distal end of infusion inlet 254. Distal end of infusion inlet 254 is advanced into end 242 of tubule 240 until pinch ring 262 is inserted in tubule 240. As shown in FIG. 10c, casing 251 of filling means 250 is advanced over end 242 of tubule 240 whereby pinch ring 262 creates an interference fit between filling tube 252 and end 242 of tubule 240. Exhaust vent 258 connects to end 244 of tubule 240 in the same manner.

Figure 12A:
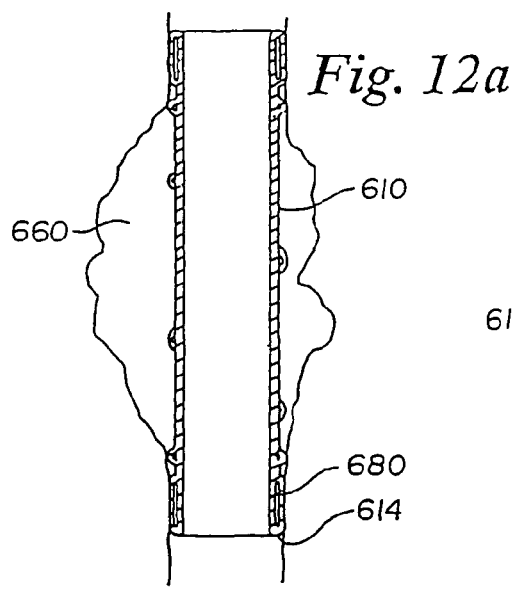
FIGS. 12a and 12b are cross sectional views of a vascular graft according to the present invention.
Figure 12B:
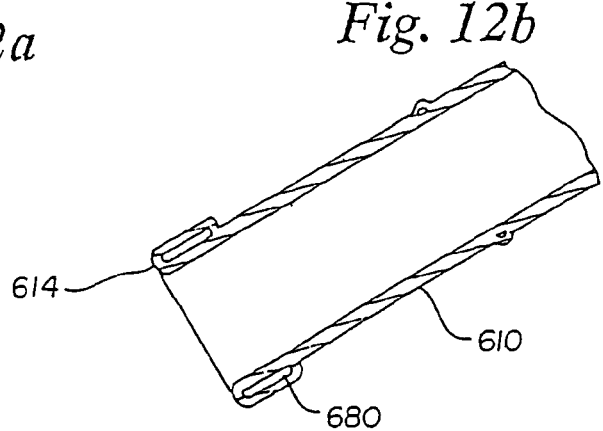

FIGS. 11-12 show alternative embodiments of the inventive vascular graft. FIG. 11a shows a graft 310 having an outer layer 370 surrounding tubules 340. FIG. 11b shows graft 310 having two outer layers 370, 372 surrounding tubules 340. FIG. 11c shows graft 410 having no outer layer over tubules 440, and lacking connection between tubule 440 and proximal coil 480. FIG. 11d shows a cross section of graft 510, having an inner core 590. FIGS. 12a and 12b show a longitudinal cross section of graft 610 in place in repair site 660, wherein graft 610 has an enlarged proximal coil 680 located directly at proximal end 614 of graft 610, i.e. not more than about 5 mm from proximal end 614.

The unique features of the device are the manner of its delivery and fixation at the site of repair, its low profile which may prevent interference with normal heart functions, and the non-invasive nature of the delivery which would reduce costs normally associated with closure of such a defect. The device and method of fixation provides a non-invasive treatment of aortic aneurysms and the like. The device is made of polymeric material and is delivered via catheter in a non-invasive procedure. In one embodiment, the device operates through chemical means to repair an aneurysm.

Advantages of the apparatus and method of the present invention are many. No preformed stent is required and the apparatus has a smaller insertion diameter than previous vascular grafts. Further, the vascular graft has a lower cost of production than previous graft materials and procedures.

The practice of the present invention achieves several objectives and advantages. Currently, there are no percutaneous devices available to cure a septal defect or the like. The device and method of the present invention provides an advantage over surgery in that the cost of the procedure is substantially less, the risk of infection is less, the hospital residency time is less and there is no physically deforming scar.

Further advantages include applicability to procedures such as repair of PDA, patent ductus anomaly. The non-invasive mode of delivery would reduce costs associated with this type of procedure. In addition, the low profile of the apparatus may minimize or prevent interference with normal heart functions.

While this invention may be embodied in many different forms, there are described in detail herein specific preferred embodiments of the invention. This description is an exemplification of the principles of the invention and is not intended to limit the invention to the particular embodiments illustrated.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. An expandable stent for insertion into a passage, said expandable stent comprising:

a body having a longitudinal axis and formed of at least one flexible sheet material comprising a woven fabric, said body being convertible from a collapsed condition in which the body is of a size to be inserted into the passage into an expanded condition in which the body is fixed relative to the passage;

a first channel disposed circumferentially and transversely about the body and extending over at least a region of the body, wherein the first channel is located at a first end of the body;

a second channel disposed circumferentially and transversely about the body and extending over at least a region of the body, wherein the second channel is located at a second end of the body;

a plurality of spaced apart channels disposed transversely about the body and extending over at least a region of the body, said plurality of channels in communication with one another, the spaced apart channels located between the first channel and the second channel;

a main channel extending axially between the first channel and the second channel, wherein the main channel is in communication with the first channel, the second channel, and the plurality of spaced apart channels, wherein the first channel, the second channel, and the plurality of spaced apart channels extend transversely from said main channel; and an inlet communicating with the first channel, wherein to enable a hardening material is introduced through the inlet and into at least the first channel so that at least said region of said body can be hardened with the hardening material to maintain the body in its expanded condition.

2. The stent of claim 1, wherein said at least one flexible sheet material is tubular or includes a tubular region.

3. The stent of claim 1, wherein the inlet is closable.

4. The stent of claim 1, further comprising a filler communicating with at least the first channel via the inlet.

5. The stent of claim 1, wherein the body comprises a sidewall which fixedly engages with a sidewall of the passage in use.

6. The stent of claim 1, wherein the channels are disposed inwardly or outwardly of said at least one flexible sheet material or between multiple flexible sheets when more than one is provided.

7. An expandable stent for insertion into a passage, said expandable device comprising:

a. a body formed of at least one flexible material comprising a woven fabric, said body being convertible from a collapsed condition in which the body is of a size to be inserted into the passage into an expanded condition in which the body is fixed relative to the passage, said body having an outer surface, a longitudinal axis, a first end and a second end;

b. a plurality of channels disposed circumferentially over the outer surface of the body and transversely to the longitudinal axis of the body, extending over at least a region of the body, and being spaced by portions of the body, wherein the plurality of channels comprises a first channel located at the first end of the body, a second channel located at the second end of the body, and a plurality of spaced apart channels between the first channel and the second channel;

c. a main channel extending axially between the first channel and the second channel, wherein the main channel is in communication with the first channel, the second channel, and the plurality of spaced apart channels, wherein the first channel, the second channel, and the plurality of spaced apart channels extend transversely from said main channel;

d. an inlet communicating with the first channel; and e. flowable rigidifying material introducible into at least the first channel, the material rigidifying within at least the first channel to thereby maintain the body in the expanded condition.

8. A stent as claimed in claim 7, wherein the inlet is closable.

9. A stent as claimed in claim 7, wherein the body comprises a sidewall which fixedly engages with a sidewall of the passage in use.

10. A stent as claimed in claim 7, wherein the plurality of channels are disposed inwardly or outwardly of said at least one flexible sheet material or between the flexible sheet materials when more than one is provided.

11. The expandable stent of claim 7, wherein the flowable rigidifying material comprises at least one component selected from the following group:
   a. a polymerizable monomer; and
   b. a pre-polymer.

12. The expandable stent of claim 7, wherein the flowable rigidifying material includes at least one of:
   a. epoxides; and
   b. acrylates.

13. The expandable stent of claim 7, wherein the flowable rigidifying material comprises at least two components wherein the components rigidify after their combination occurs.

14. A stent for insertion in a body passage comprising:
   a tubular member having an outer surface, a longitudinal axis, a first end and a second end and formed of a woven fabric, the woven fabric having a first condition in which said woven fabric is collapsed and a second condition in which said woven fabric is expanded to conform to a shape of at least a part of said passage when said woven fabric is disposed within said passage; a plurality of flexible channels formed from the woven fabric and disposed circumferentially over the tubular member and transversely to the longitudinal axis, said channels including a first channel at the first end of the woven fabric, a second channel at the second end of the woven fabric, and a plurality of spaced apart channels between the first channel and the second channel; and a main channel extending axially between the first channel and the second channel, the main channel axially aligned with the longitudinal axis, the main channel in fluid communication with the first channel, the second channel, and the plurality of spaced apart channels, the plurality of spaced apart channels transversely extending from said main channel, wherein said channels have a flowable rigidifying material therein, and wherein rigidification of the material fixes said channels in said second condition.

15. The stent of claim 14, wherein said woven fabric includes two superimposed sheets, said sheets having sealed regions and unsealed regions, said sheets being joined along said sealed regions and forming said channels in said unsealed regions.

16. The stent of claim 14, wherein said channels form ridges along said unsealed regions when filled with said rigidifying matter, said ridges being adapted to engage said passage to maintain said device within said passage.

17. The stent claim 14, wherein said channels include an inlet adapted to receive said rigidifying material, and wherein said main channel is in communication with said inlet.

18. An expandable stent for insertion into a lumen, the stent comprising:
   a body formed of flexible material comprising a woven fabric and having a longitudinal axis, a first end, a second end, and an outer surface;
   the stent being convertible;
      (1) from a collapsed condition wherein the stent is insertable into the lumen;
      (2) into an expanded condition wherein the stent extends over and supports the surface of the lumen, and wherein the stent at least partially encircles an interior passage extending along the lumen; and
   the stent further having areas thereon spaced by expandable channels, said expandable channels including a main channel axially aligned with the longitudinal axis, the main channel in communication with subsidiary channels disposed circumferentially over the outer surface of the body and extending transversely from said main channel, a first subsidiary channel at the first end of the body, a second subsidiary channel at the second end of the body, and a plurality of spaced apart subsidiary channels between the first subsidiary channel and the second subsidiary channel, wherein the expandable channels have fluid rigidifying material therein which maintains the stent in the expanded condition, the material rigidifying to fix the device in the expanded condition.

19. The expandable stent of claim 18, wherein the expandable channels have widths shorter than the spacing between the expandable channels.

20. The expandable stent of claim 18, wherein the expandable channels, when expanded, define a framework of at least substantially tubular shape.

21. The expandable stent of claim 18, wherein the expandable channels extend about the interior passage in at least a substantially circumferential direction.

22. The expandable stent of claim 18, wherein the stent is tubular with the interior passage extending therein between opposing ends of the stent, the interior passage being collapsed when the stent is in its collapsed condition.

* * * * *